US011118209B2

(12) United States Patent
Moriwaki et al.

(10) Patent No.: US 11,118,209 B2
(45) Date of Patent: Sep. 14, 2021

(54) DEVICE FOR DETERMINING LIVE/DEAD BACTERIAL STATE AND METHOD FOR DETERMINING LIVE/DEAD BACTERIAL STATE USING THE DEVICE

(71) Applicant: NIHON RIKAGAKU KAIHATSU LLC., Fukuoka (JP)

(72) Inventors: Toshikazu Moriwaki, Fukuoka (JP); Hideki Moriwaki, Fukuoka (JP)

(73) Assignee: NIHON RIKAGAKU KAIHATSU LLC., Fukuoka (JP)

( * ) Notice: Subject to any disclaimer, the term of this patent is extended or adjusted under 35 U.S.C. 154(b) by 237 days.

(21) Appl. No.: 15/778,877

(22) PCT Filed: Dec. 26, 2016

(86) PCT No.: PCT/JP2016/088798
§ 371 (c)(1),
(2) Date: May 24, 2018

(87) PCT Pub. No.: WO2017/115768
PCT Pub. Date: Jul. 6, 2017

(65) Prior Publication Data
US 2018/0346956 A1    Dec. 6, 2018

(30) Foreign Application Priority Data

Dec. 28, 2015  (JP) .............................. JP2015-257250

(51) Int. Cl.
*C12Q 1/06*    (2006.01)
*C12Q 1/02*    (2006.01)
(Continued)

(52) U.S. Cl.
CPC ................. *C12Q 1/06* (2013.01); *C12M 1/12* (2013.01); *C12M 1/34* (2013.01); *C12Q 1/02* (2013.01)

(58) Field of Classification Search
CPC .......... C12M 41/06; C12M 41/46; C12Q 1/06; C12Q 1/02
See application file for complete search history.

(56) References Cited

U.S. PATENT DOCUMENTS 4,807,984 A * 2/1989 Kurimura ........ G01N 35/00029
359/391
5,364,790 A   11/1994 Atwood et al.
(Continued)

FOREIGN PATENT DOCUMENTS

CN    1095759 A    11/1994
CN    1717693 A    1/2006
(Continued)

OTHER PUBLICATIONS

JP 2008187935A English translation (Year: 2008).*
(Continued)

*Primary Examiner* — Nathan A Bowers
(74) *Attorney, Agent, or Firm* — Lucas & Mercanti, LLP

(57) ABSTRACT

Provided is a device for determining the live/dead bacterial state, with which it is possible to ascertain the accurate state of live bacteria/dead bacteria via a captured image in a relatively easy operation with which ascertaining the state of a bacterial cell is more accurate than conventional methods. This device for determining the live/dead bacterial state comprises: a case body in which a measurement mechanism is housed; an opening/closing lid body that allows a fungus base insertion port formed in the case body to be opened and closed; and the measurement mechanism, which is housed in the case body and is configured to measure the number of bacteria. The measurement mechanism comprises: a fungus base holding mechanism that inserts and fixes a fungus base on which a bacterial cell collected from a specimen is placed; an excitation light irradiating mechanism configured so as to be capable of focusing and irradiating an excitation (Continued)

light toward the bacterial cell on the fungus base; an imaging camera disposed above the bacterial cell on the fungus base; and an XY-axes adjustment mechanism that minutely adjusts and moves, in the XY-axes, an XY stage supporting the fungus base holding mechanism and comprising two separately moving layers.

9 Claims, 11 Drawing Sheets

(51) Int. Cl.
*C12M 3/00* (2006.01)
*C12M 1/12* (2006.01)
*C12M 1/34* (2006.01)

(56) References Cited

U.S. PATENT DOCUMENTS

| | | | | |
|---|---|---|---|---|
| 8,889,351 | B2* | 11/2014 | Mach | C12Q 1/04 435/6.1 |
| 2003/0003527 | A1* | 1/2003 | Shimakita | G01N 33/582 435/34 |
| 2003/0155528 | A1* | 8/2003 | Tokuda | C12Q 1/04 250/461.2 |
| 2005/0105172 | A1* | 5/2005 | Hasegawa | C12M 23/50 359/368 |
| 2006/0166305 | A1* | 7/2006 | Jiang | C12M 41/36 435/29 |
| 2009/0263782 | A1* | 10/2009 | Ward | G01N 21/253 435/3 |
| 2010/0129852 | A1* | 5/2010 | Putnam | C12Q 1/24 435/29 |
| 2012/0016230 | A1 | 1/2012 | Kishima et al. | |
| 2012/0099107 | A1* | 4/2012 | Ahn | G01B 11/02 356/400 |
| 2012/0235036 | A1* | 9/2012 | Hatakeyama | H01J 37/073 250/310 |
| 2013/0217107 | A1 | 8/2013 | Pederson et al. | |

FOREIGN PATENT DOCUMENTS

| | | |
|---|---|---|
| CN | 102370462 A | 3/2012 |
| JP | 09-275998 A | 10/1997 |
| JP | 2000232897 A | 8/2000 |
| JP | 2003169695 A | 6/2003 |
| JP | 2006-029793 A | 2/2006 |
| JP | 2008054509 A | 3/2008 |
| JP | 2008187935 A | 8/2008 |
| JP | 2014502856 A | 2/2014 |
| WO | 02/064818 A1 | 8/2002 |
| WO | 2004/051554 A1 | 6/2004 |

OTHER PUBLICATIONS

English translation of JP 2008-187935A to Horikiri et al (generated 2020).*

EPO, Extended European Search Report for the corresponding European Patent Application No. 16881743.5, dated Jun. 12, 2019 (7 pages).

International Search Report dated Apr. 18, 2017 for PCT/JP2016/088798 and English translation.

CNIPA, Office Action for the corresponding Chinese Patent Application No. 201680065793.2, dated Mar. 2, 2021, with English translation.

* cited by examiner

| NUMBER OF FUNGUS | PROCESS |
|---|---|
| MANY | TRANSMITTING DIMMING SIGNAL |
| MEDIUM | DOING NOTHING |
| FEW | TRANSMITTING BOOSTING SIGNAL |

| LUMINANCE | PROCESS |
|---|---|
| HIGH LUMINANCE | TRANSMITTING DIMMING SIGNAL |
| MEDIUM LUMINANCE | DOING NOTHING |
| LOW LUMINANCE | TRANSMITTING BOOSTING SIGNAL |

FIG. 12

|  | MANY IN NUMBER OF FUNGUS | MEDIUM IN NUMBER OF FUNGUS | FEW IN NUMBER OF FUNGUS |
|---|---|---|---|
| HIGH LUMINANCE | TRANSMITTING DIMMING SIGNAL | TRANSMITTING DIMMING SIGNAL | DOING NOTHING |
| MEDIUM LUMINANCE | TRANSMITTING DIMMING SIGNAL | DOING NOTHING | TRANSMITTING BOOSTING SIGNAL |
| LOW LUMINANCE | SETTING ON TO MULTIPLE SHOOTING FLAG | TRANSMITTING BOOSTING SIGNAL | TRANSMITTING BOOSTING SIGNAL |

FIG. 13

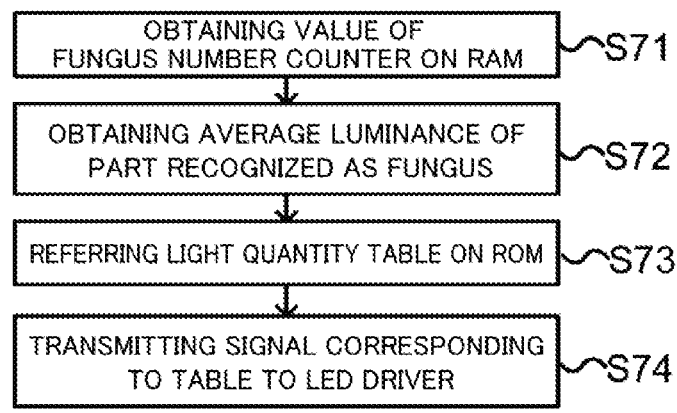

DEVICE FOR DETERMINING LIVE/DEAD BACTERIAL STATE AND METHOD FOR DETERMINING LIVE/DEAD BACTERIAL STATE USING THE DEVICE

CROSS REFERENCE TO RELATED APPLICATION

This Application is a 371 of PCT/JP2016/088798 filed on Dec. 26, 2016 which, in turn, claimed the priority of Japanese Patent Application No. 2015-257250 filed on Dec. 28, 2015, both applications are incorporated herein by reference.

BACKGROUND OF THE INVENTION

1. Field of the Invention

The present invention relates to a device capable of determining a live bacterial state and a dead bacterial state of fungus collected from a specimen in which bacteria or mold is adhered or mixed (hereinafter, collectively called as fungus), and especially to a device extremely suitable for producers or distributors of foods, through which determination of fungus can be done immediately.

2. Description of Related Art

Foods, in particular, fresh food or processed food, etc. with high moisture percentage has a condition under which breeding of fungus is easy to occur, therefore it concludes that such fungus, etc. is mixed at a production primitive stage of foods or mixed when dropped down and such fungus breeds in a short time, thus extremely becomes unsanitary, and further food poisoning is often invited or deterioration or corruption of product is invited.

Accordingly, although flesh food is wrapped by a container made of synthesized resin material or paperware and further cold insulation is given, thereafter is provided for circulation or consumption, since antibacterial treatment is not conducted for such container or paperware, not only fungus mixed at the production primitive state breeds with the passage of time but also fungus adhered during circulation or consumption or when dropped down breeds on an outer surface of the container or paperware, thus such flesh food is placed in an extremely unsanitary state.

On the other hand, as for the processed food, although it is attempted that synthetic preservatives conventionally permitted is added and fungus is prevented from breeding, it concludes that synthetic preservatives is regarded as dangerous based on recent increase in health consciousness. Therefore, additionally coupled with Product Liability, that is, enforcement of PL law from the standpoint of consumer protection, it is fact that sanitation management is strongly desired for not only food producers but also distributors.

Taking the above situation into consideration, it is recently appears a technology that collected fungus is inoculated on coloring medium in which coloring component, for example, such as X-Gal is appropriately mixed and this is cultivated for 24 hours to 48 hours in an incubating container such as incubator retained at a required temperature, thereby colony is formed and the coloring component is decomposed and colored by β-galactosidase enzyme retained by $E.\ coli$, etc., thereby fungus is determined.

However, this technology has a disadvantage that it requires a long time for cultivation to determine fungus as determining means of fungus in foods used for distribution and is poor for practical use, and determinable fungus is limited to a part of $E.\ coli$ and general viable bacteria and further it cannot be determined live bacteria/dead bacteria.

Further, it is also proposed a method as another determining technology that collected fungus is mixed in coloring solution in which fluorescent dye is mixed in physiological saline with an appropriate concentration and this is cultivated for 24 hours to 48 hours and colony is formed, thereafter fungus is determined by optical microscope.

However, there are many problems that this method also requires a long time for cultivation and cells are not colored enough since fluorescent dye is hard to enter in cells of fungus and dye penetrated in cells is easy to leak, therefore light emission energy is weak, thus determination device necessary to use precision high magnification lens becomes large size and high cost. As mentioned, there are many problems to determine fungus of foods used for distribution.

Taking these problems into consideration, as disclosed in Japanese Patent No. 2979383, it is investigated that: fluorescent dye made of fluorescein or derivatives thereof is easy to penetrate in both live bacteria cells and dead bacteria cells; fluorescent dye made of propidiumiodide can penetrate only in the cells of dead bacterial; fluorescent dye made of fluorescein or derivatives thereof penetrated in the cells of live bacteria absorbs excitation light with a specific wavelength of 480 nm and indicates strong fluorescence emission with a wavelength of 520 nm which is longer than that of absorbed light according to the Stoke's law; fluorescent dye made of propidiumiodide penetrated in the cells of dead bacteria indicates strong fluorescent emission with a 625 wavelength longer than that of absorbed light according to Stoke's law, based on adsorption of excitation light with a 488 nm wavelength, on the other hand, fluorescent dye made of fluorescein or derivatives thereof is captured in the cells of dead bacteria and fluorescent emission is inhibited. On the basis of this, it is proposed in Japanese Unexamined Patent Application Publication No. H09-275998 a technology through which it can be immediately determined an emission number every wavelength of fluorescent light (live bacteria and dead bacteria), an emission shape (kind of bacteria) and an emission number (bacteria number), etc. with low magnification by making light scattering without cultivation of colored fungus solution colored by fluorescent dye based on that emission energy conducting fluorescent emission by absorbing excitation light with a specific wavelength of 488 nm is extremely strong.

By this technology, fungus deposited and collected by appropriate means from specimen on which fungus such as bacteria or molds are mixed and adhered can be immediately determined as live bacteria and dead bacterial, kind of bacterial or number of bacteria, by an extremely simple method.

However, although the technology to determine the live bacterial state and the dead bacterial state or the other state is a basic technology capable of immediately determining results, since the emission number every wavelength of fluorescent light, the emission shape, the emission number, etc. are viewed through magnifying lens, process work to actually obtain such determined results has expertise and is not easy to execute for everyone, and further lacks accuracy due to that viewing technology is done by using magnifying lens.

That is, although the above technology is an excellent technology to distinguish the live bacteria and the dead bacterial by using fluorescent emission to determine fungus, viewing determination is finally conducted. Therefore, works coming to viewing become complex and understanding situation of fungus becomes inaccurate. Further, images become indefinitely since fungus state is visually confirmed through the magnifying lens when viewing is conducted, thus there is disadvantage that accurate understanding situation of live bacteria and the dead bacteria becomes difficult.

SUMMARY OF THE INVENTION

The present invention has solved the above problems as a device for determining a live/dead bacterial state based on that staining bacterial solution is prepared as advance preparation and is dropped on a filter, excitation light is accurately irradiated from diagonally above onto the staining bacterial solution on the filter through a plurality of LEDs for excitation light, fungus of the live bacteria and the dead bacteria is made emit light with a predetermined fluorescent wavelength, fungus is imaged by CMOS image sensor, thereby fungus can be accurately imaged.

That is, the present invention relates to a determination device for determining a live/dead bacterial state, the device comprising: a case body inside of which is made a darkroom space in which a measurement mechanism is housed; and an opening/closing lid body openable and closable a fungus base insertion port formed in front of the case body; wherein the measurement mechanism is housed in the case body and configured to determine live bacteria and dead bacteria of the fungus collected from a specimen and to measure a number of bacteria, and wherein the measurement mechanism comprises: a fungus base holding mechanism that a fungus base on which the fungus collected from the specimen is placed is inserted and fixed; an excitation light irradiation mechanism arranged in a diagonally upper periphery of the fungus base holding mechanism and constituted in capable of intensively irradiating toward the fungus on the fungus base; an imaging camera arranged above the fungus on the fungus base through a fixation frame; and an XY-axes adjustment mechanism for moving and minutely adjusting an XY stage constituted from two separately moving layers and supporting the fungus base holding mechanism in an XY-axes direction.

Further, it is characterized in that a measurement filter through which the fungus is filtered and collected from the specimen is put on a part of the fungus base.

Further, it is characterized in that a filter switching mechanism for switching a plurality of band pass filters arranged between the fungus base and the imaging camera is arranged behind a fixation frame of the imaging camera.

Further, it is characterized in that the fungus base holding mechanism is constituted from: left and right rails clamping both side edges of the fungus base from left and right outer side directions; a rail displacement mechanism for releasing clamp of the fungus base by the left and right rails through displacing one of the left and right rails toward outside; and an operation lever arranged outside of the one of the left and right rails to operate the rail displacement mechanism from the fungus base insertion port and constituted so as to be able to rotationally operate around a support portion positioned at midway of the operation lever; and the rail displacement mechanism is constituted from: a slide shaft horizontally projected on the one of the left and right rails; an operation lever contact projection formed on a head portion of the slide shaft; an operation support portion supporting a midway portion of the operation lever a top portion of which contacts with the operation lever contact projection on the XY stage; and a compression spring provided between an outer side surface of the one of the left and right rails and the top portion of the operation lever.

Further, it is characterized in that the excitation light irradiation mechanism includes a plurality of excitation light LEDs arranged in a diagonally upper periphery of the fungus base holding mechanism and each excitation light LED is alternately arranged by dividing the LEDs for live bacteria and for dead bacteria.

Further, it is characterized in that in the imaging camera the fungi on the measurement filter are distinguished into a predetermined number of grid sections and an image process is conducted by a computer separately connected through light grasped by a CMOS image sensor every grid section.

Further, it is characterized in that in the XY-axes adjustment mechanism each of output shafts in an X axis motor and a Y axis motor is interlocked and concatenated to the XY stage with two layers, and an origin position is set on the XY stage beforehand and movement distance information centering the origin position is transmitted to a control portion of each of the X axis motor and the Y axis motor and correction of the origin is conducted when the XY stage with two layers is moved and minutely adjusted in the XY-axes direction.

Further, it is characterized in that a step for filtering and collecting the fungus on the measurement filter comprises steps of:

a step 1 for dropping small amount of the specimen in a test tube;

a step 2 for dropping special reagent in the test tube and for sealing and standing the test tube still after stirring;

a step 3 for housing and setting the measurement filter in a filter housing separately provided;

a step 4 for connecting the filter housing in which the measurement filter is housed to a top portion of a syringe separately provided and forming a communication state between inner side of the filter housing and inner side of the syringe;

a step 5 for injecting the specimen in the test tube into the inner side of the syringe;

a step 6 for pressing the inner side of the syringe and pressing in the fungus together with the specimen toward the measurement filter in the filter housing from the top portion of the syringe, thereby for filtering and collecting only fungus stained on a surface of the measurement filter;

a step 7 for taking out the measurement filter from the filter housing and putting the measurement filter on the fungus base, thereby for arranging the fungi filtered and collected on the surface of the measurement filter on the fungus base through the measurement filter; and a step 8 for inserting the fungus base in the fungus base holding mechanism provided in the determination device for determining a live/dead bacterial state and for determining the live/dead bacterial state by utilizing the excitation light irradiation mechanism and the imaging camera provided in the determination device and grasping a fungus state as images.

Effects of Invention

According to the determination device for determining a live/dead bacterial state, the determination device is constituted from a case body inside of which is made a darkroom space in which a measurement mechanism is housed; and an opening/closing lid body openable and closable a fungus base insertion port formed in front of the case body; wherein the measurement mechanism is housed in the case body and configured to determine live bacteria and dead bacteria of the fungus collected from a specimen and to measure a number of bacteria, and wherein the measurement mechanism comprises: a fungus base holding mechanism that a fungus base on which the fungus collected from the specimen is placed is inserted and fixed; an excitation light irradiation mechanism arranged in a diagonally upper periphery of the fungus base holding mechanism and constituted in capable of intensively irradiating toward the fungus on the fungus base; an imaging camera arranged above the fungus on the fungus base through a fixation frame; and an XY-axes adjustment mechanism for moving and minutely adjusting an XY stage constituted from two separately moving layers and supporting the fungus base holding mechanism in an XY-axes direction. Thereby, in spite of comparative easy operation, the fungus state can be accurately grasped in comparison with the conventional operation. Further, the fungus state of the live bacteria and the dead bacteria can be accurately grasped through the images shot in the above.

Further, a measurement filter through which the fungus is filtered and collected from the specimen is put on a part of the fungus base. Thereby, the live/dead bacteria trapped on the filter can be directly determined, and moreover since the filter is put on the fungus base, the filter becoming the specimen can be easily moved together with the fungus base.

Further, a filter switching mechanism for switching a plurality of band pass filters arranged between the fungus base and the imaging camera is arranged behind a fixation frame of the imaging camera. Thereby, the filter switching mechanism can be compactly housed within the case body.

Further, the fungus base holding mechanism is constituted from: left and right rails clamping both side edges of the fungus base from left and right outer side directions; a rail displacement mechanism for releasing clamp of the fungus base by the left and right rails through displacing one of the left and right rails toward outside; and an operation lever arranged outside of the one of the left and right rails to operate the rail displacement mechanism from the fungus base insertion port and constituted so as to be able to rotationally operate around a support portion positioned at midway of the operation lever; the rail displacement mechanism is constituted from: a slide shaft horizontally projected on the one of the left and right rails; an operation lever contact projection formed on a head portion of the slide shaft; an operation support portion supporting a midway portion of the operation lever a top portion of which contacts with the operation lever contact projection on the XY stage; and a compression spring provided between an outer side surface of the one of the left and right rails and the top portion of the operation lever. Thereby, set and removal of the fungus base can be easily done, moreover the fungus base can be firmly held in the measurement state.

Further, the excitation light irradiation mechanism includes a plurality of excitation light LEDs arranged in a diagonally upper periphery of the fungus base holding mechanism and each excitation light LED is alternately arranged by dividing the LEDs for live bacteria and for dead bacteria. Thereby, the excitation light irradiated from each of the excitation light LEDs is not inhibited by the fungus base or the filter, etc., therefore, the fungus on the filter can be directly irradiated and effective fluorescence emission can be promoted. Further, based on that the excitation LEDs for live bacteria and for dead bacteria are alternately arranged, the excitation light can be uniformly irradiated for the fungus on the filter.

Further, in the imaging camera the fungi on the measurement filter are distinguished into a predetermined number of grid sections and an image process is conducted by a computer separately connected through light grasped by a CMOS image sensor every grid section. Thereby, in comparison with a case that the number of live bacteria and dead bacteria is visually counted by direct speculum, the state determination can be accurately conducted while dramatically reducing effort and can be stably conducted without individual difference of the measurer.

Further, in the XY-axes adjustment mechanism each of output shafts in an X axis motor and a Y axis motor is interlocked and concatenated to the XY stage with two layers, and an origin position is set on the XY stage beforehand and movement distance information centering the origin position is transmitted to a control portion of each of the X axis motor and the Y axis motor and correction of the origin is conducted when the XY stage with two layers is moved and minutely adjusted in the XY-axes direction. Thereby, the fungus base holding mechanism on the XY stage can be moved in the XY-axes direction and the state can be determined while accurately retaining reproducibility every measurement.

Further, a step for filtering and collecting the fungus on the measurement filter comprises steps of: a step 1 for dropping small amount of the specimen in a test tube; a step 2 for dropping special reagent in the test tube and for sealing and standing the test tube still after stirring; a step 3 for housing and setting the measurement filter in a filter housing separately provided; a step 4 for connecting the filter housing in which the measurement filter is housed to a top portion of a syringe separately provided and forming a communication state between inner side of the filter housing and inner side of the syringe; a step 5 for injecting the specimen in the test tube into the inner side of the syringe; a step 6 for pressing the inner side of the syringe and pressing in the fungus together with the specimen toward the measurement filter in the filter housing from the top portion of the syringe, thereby for filtering and collecting only fungus stained on a surface of the measurement filter; a step 7 for taking out the measurement filter from the filter housing and putting the measurement filter on the fungus base, thereby for arranging the fungi filtered and collected on the surface of the measurement filter on the fungus base through the measurement filter; and a step 8 for inserting the fungus base in the fungus base holding mechanism provided in the determination device for determining a live/dead bacterial state and for determining the live/dead bacterial state by utilizing the excitation light irradiation mechanism and the imaging camera provided in the determination device and grasping a fungus state as images. Thereby, in spite of comparative easy operation, the fungus state can be accurately grasped in comparison with the conventional operation. Further, the fungus state of the live bacteria and the dead bacteria can be accurately grasped through the images shot in the above.

BRIEF DESCRIPTION OF THE DRAWINGS

FIG. 12 is an explanatory view showing a light quantity table.

FIG. 13 is a flowchart showing processes executed in the control portion.

DETAILED DESCRIPTION

Figure 1:
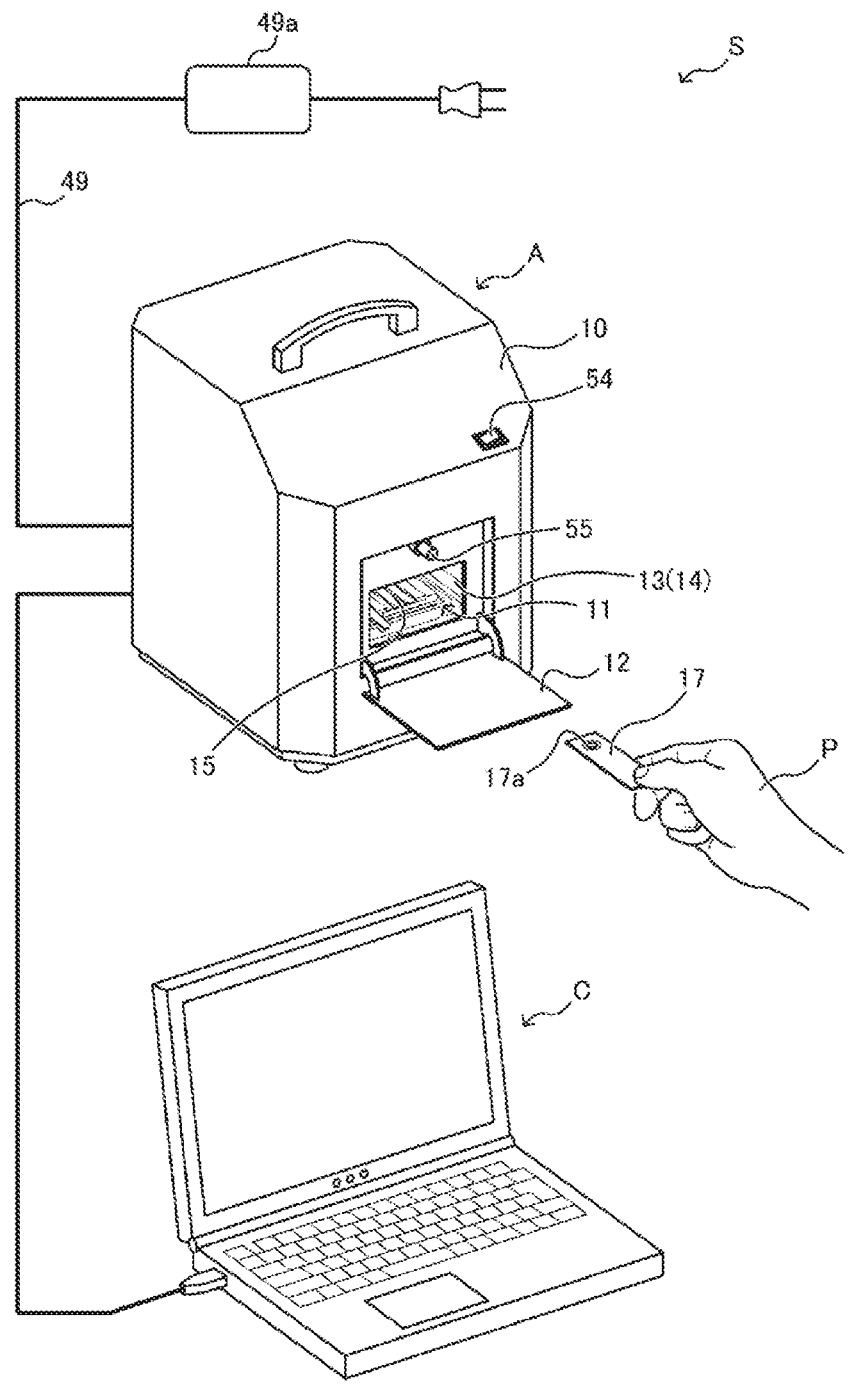
FIG. 1 is an explanatory view showing a constitution of a state determination system.

Hereinafter, a device for determining a live/dead bacterial state and a method for determining a live/dead bacterial state according to the present embodiment will be described with reference to the drawings. FIG. 1 is an explanatory view showing a system for determining a live/dead bacterial state, the system being constituted by electrically connecting a device for determining a live/dead bacterial state (hereafter, called as determination device A) according to the present embodiment and a computer C.

The determination device A is constituted from a case body 10 with a substantially rectangular shape and a measurement mechanism 11 housed in the case body 10.

The case body 10 is formed into a substantially sealed rectangular shape and inside thereof is made in a darkroom space. Here, to stably put this case body 10, weights are provided on a bottom of the case body 10. In a front side wall, an opening/closing lid body 12 is arranged so as to become openable and closable.

The measurement mechanism 11 is a part to determine a live/dead bacterial state and operates by power supplied from commercial power supply (not shown) through a power cable 49 during which a voltage converter 49a is provided.

When the opening/closing lid body 12 is operated to open, the measurement mechanism 11 within the case body 10 is deactivated. And when the opening/closing lid body 12 is operated to close, the measurement mechanism 11 is activated. The measurement mechanism 11 and the opening/closing lid body 12 are interlocked and concatenated.

An opening 13 opened and closed by the opening/closing lid body 12 is formed as a fungus base insertion port 14 and, within the fungus base insertion port 14, a fungus base holding mechanism 15 constituting a front portion as a part of the measurement mechanism 11 is provided.

Figure 2:
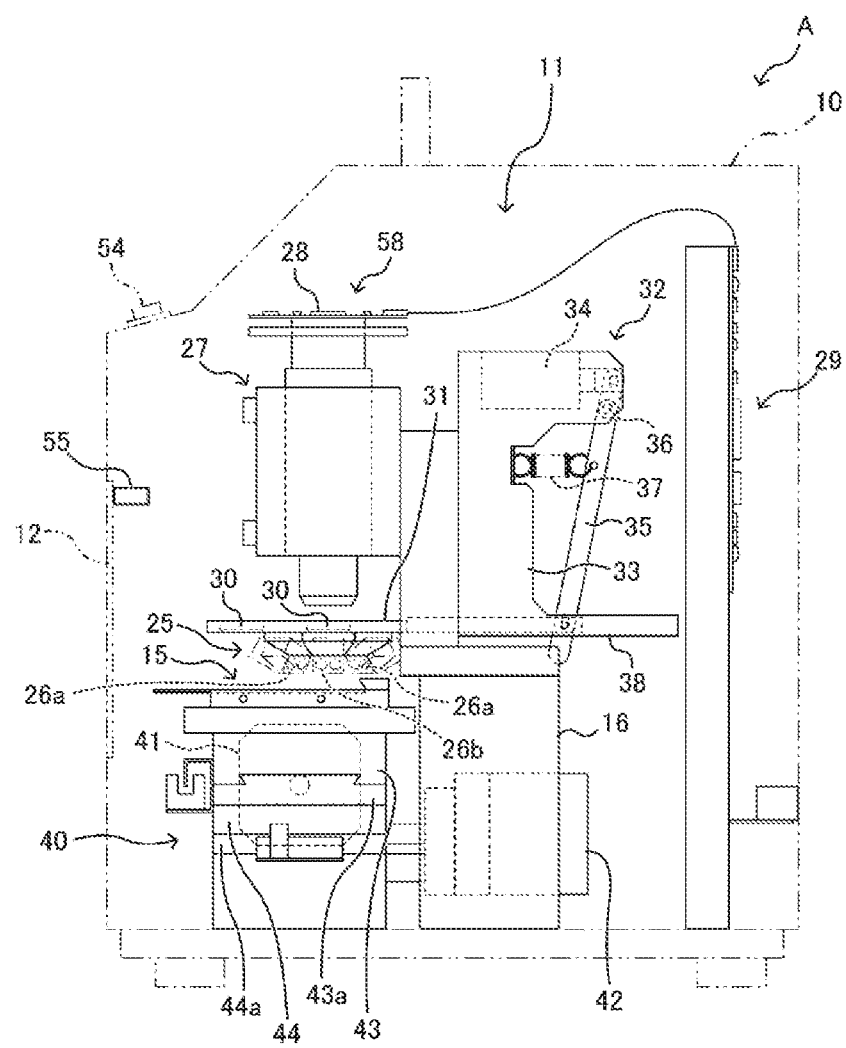
FIG. 2 is an explanatory view showing a constitution of a determination device according to the present embodiment.
Figure 3A:
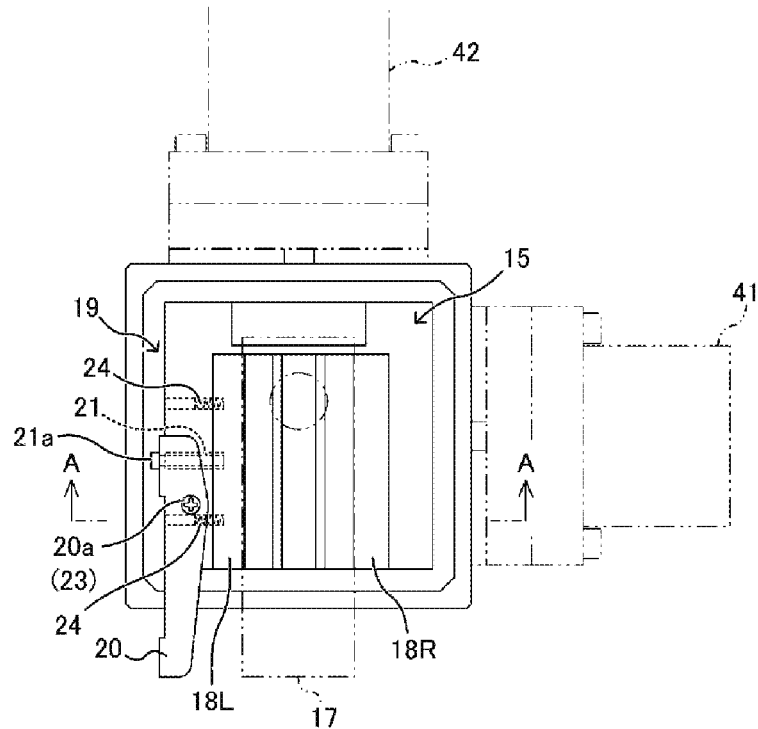
FIGS. 3A-3C are explanatory views showing a constitution of a fungus base holding mechanism and an XY stage.
Figure 3B:
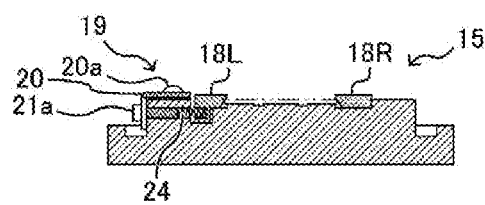
Figure 3C:
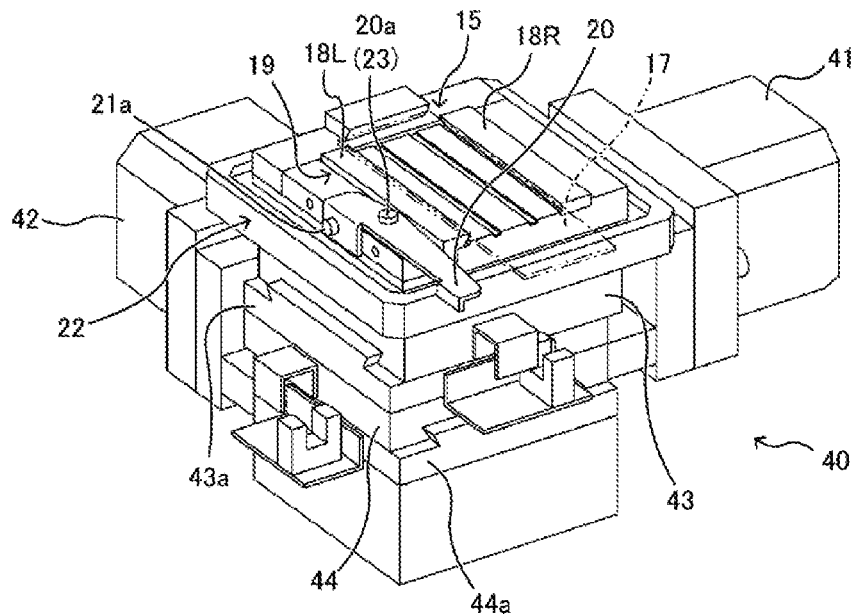

As shown FIG. 2, the fungus base holding mechanism 15 is arranged on an almost gate type of fixation frame 16 which is provided in the case body 10 and as shown in FIGS. 3A-3C, the fungus holding mechanism 15 is constituted from: a pair of left and right rails 18L, 18R clamping both longitudinal side edges of a fungus base 17 (see FIG. 1) from left and right outsides, the fungus base 17 being inserted by a user P and having a rectangular shape in a plan view; a rail displacement mechanism 19 displacing one of the left and right rails 18L, 18R (left rail 18L in the present embodiment) toward outside and releasing clamp of the fungus base 17 by the left and right rails 18L, 18R; and an operation lever 20 arranged at outside of the one of the left and right rails 18L, 18R to operate the rail displacement mechanism 19 from the fungus base insertion opening 14 and constituted so that rotational operation can be done around a support portion 20a arranged in the midway of the operation lever 20. The rail displacement mechanism 19 is constituted from: a slide shaft 21 horizontally projected from the one of the left and right rails 18L, 18R; an operation lever contact projection 21a formed on a head of the sliding shaft 21; an operational support portion 23 through which a midway of the operation lever 20 a top portion of which contacts with the operation lever contact projection 21a is supported on an XY stage 22; and a compression spring 24 arranged between outside of the one of the left and right rails 18L, 18R and the top portion of the operation lever 20.

The fungus base 17 inserted and fixed on the fungus base holding mechanism 15 has the fungus collected from the specimen thereon. Concretely, as mentioned hereinafter, the fungus collected from the specimen and treated by the fluorescent staining solution is filtered by a measurement filter 17a and collected and such measurement filter 17a itself on which the treated fungus is adhered is put on the fungus base 17, thereafter the measurement filter 17a is set on the fungus base holding mechanism 15 in the measurement mechanism 11.

Further, as shown in FIG. 2, around the fungus base holding mechanism 15, an excitation light irradiation mechanism 25 is arranged and the excitation light irradiation mechanism 25 is constituted from a plurality of excitation light LEDs 26 arranged in a diagonally upper periphery of the fungus base holding mechanism 15. Each of the excitation light LEDs 26 is alternately arranged so as to be divided into a LED 26a for live bacteria and a LED 26b for dead bacteria.

That is, totally six excitation light LEDS 26 are alternately arranged in a circular shape so as to be divided into three LEDs 26a for live bacteria and three LEDs 26b for dead bacteria.

The LED 26a for live bacteria uses a light emitting diode (LED) capable of irradiating blue excitation light including wavelength of 488 nm and the LED 26b for dead bacteria uses a light emitting diode (LED) capable of emitting green excitation light including wavelength of 530 nm. Each excitation light LED 26 is constituted so that the excitation light can be intensively irradiated from diagonal upper periphery toward the measurement filter 17a on which the treated fungus is adhered. In other words, each excitation light LED 26 is arranged in circular shape so as to enclose the measurement filter 17a in the upper area of the measurement filter 17a and is constituted so that multiple excitation light irradiation can be conducted from diagonal upper periphery toward the fungus on the measurement filter 17a.

Further, on the fixation frame 16, at an upper position of the measurement filter 17a on which the fungus treated by the staining solution is adhered, it is arranged an imaging camera 27 oriented to the measurement filter 17a through an inner space of each excitation light LED 26 arranged in a circular shape.

The imaging camera 27 transmits a light receiving signal to a control portion 29 arranged at a rear part of the measurement mechanism 11 by distinguishing the fungi on the measurement filter 17a into a predetermined number of latticework sections and by light received every section through a CMOS image sensor 28. In the control portion 29, image analysis process is conducted by pattern matching method and image data and analysis result are transmitted to the computer C.

Concretely, the imaging camera 27 possesses an optical system to enlarge the fungus on the measurement filter 17a to the extent that the fungus can be individually determined and the imaging camera 27 respectively images the fungus adhered on the measurement filter 17a every virtual section of 24 frames which is virtually sectioned by, for example, moving the measurement filter 17a in the XY axes direction of 24 frames through an XY stage 22 mentioned later, without imaging the entire measurement filter 17a by one frame all at once.

In terms of results, an imaging point of the imaging camera 27 is that the imaging camera 27 virtually distinguishes an area with a diameter of 1 cm in the measurement filter 17a into 24 frames and images every section respectively distinguished. For that reason, the measurement filter 17a is moved in the XY axes direction by the XY stage 22.

Between the imaging camera 27 and the measurement filter 17a, a band pass filter 30 is arranged to remove miscellaneous ray so that unnecessary excitation light or miscellaneous ray is not mixed and not imaged when fluorescence is received.

The band pass filter 30 is constituted by arranging two kinds of circle filters for live bacteria and dead bacteria on a rectangular frame 31 back and forth.

The two kinds of band pass filters 30 on the frame 31 are switched through a filter switching mechanism 32 which is switchable corresponding to imaging of live bacteria and dead bacteria.

The filter switching mechanism 32 is constituted from: a switching solenoid 34 arranged on a top end of a switching frame 33 installed on the fixation frame 16; a drive arm 35 supported and connected to a top of a plunger of the switching solenoid 34; a support portion 36 supporting the midway of the drive arm 35 to the switching frame 33; a spring 37 arranged between the drive arm 35 and the switching frame 33 under the support portion 36; an operation arm 38 movable in the front and back direction, a midway of the operation arm 38 and a lower end of the drive arm 35 being supported and connected; and the frame 31 possessing the band pass filter 30 which is concatenated at a front end of the operation arm 38.

Therefore, based on electrical advance/retreat operation of the solenoid, the band pass filter 30 concatenated and connected through a link mechanism of the drive arm 35, the operation arm 38, the support portion 36 and the like is constituted so that two kinds of filters can be arranged between the imaging camera 27 and the measurement filter 17a by switching forth and back movement, thereby it is prevented excitation light or unnecessary miscellaneous ray from being mixed.

An XY axes adjustment mechanism 40 is for conducting XY movement to image the fungus base holding mechanism 15 on which the measurement filter 17a is arranged with, for example, 24 frames. As shown in FIG. 3C, the XY-axes adjustment mechanism 40 is constituted so that each output shaft of an X-axis motor 41 and a Y-axis motor 42 is respectively interlocked and concatenated to the two layer XY stage 22, an origin position is set for the XY stage 22 beforehand and when the two layer XY stage 22 is finely adjusted and moved in the XY-axes direction, movement distance information centering at the origin is transmitted to a control portion of each X-axis motor 41, Y-axis motor 42 and origin correction is conducted, thereafter the XY stage 22 is moved.

That is, an X board 43 sliding in the X axis direction and a Y board 44 sliding in the Y axis direction are layered in the two layers state under a state that each board independently moves.

The X board 43 is constituted so as to be able to slide in the X axis direction through a screw mechanism or a predetermined drive mechanism including rack, pinion, etc. for the drive shaft of the X-axis motor 41.

Under the X board 43, the Y board 44 is constituted so as to be able to slide in the Y-axis direction through a predetermined drive mechanism for the drive shaft of the Y-axis motor 42.

By driving the X axis motor 41, the X board 43 is moved in the X-axis direction and, under the X board 43, the Y board 44 on an upper surface of which the X board 43 is put on is integrally moved in the Y-axis direction together with the X board 43 on the upper surface thereof when the Y board 44 is moved in the Y-axis direction. Further, the Y board 44 is moved and adjusted from the origin of the X, Y boards 43, 44, thereby positional adjustment against an imaging point is conducted by moving amount corresponding to 24 frames.

Here, it is constituted that movement of the X board 43 integral with the Y board 44 is done together with the X axis motor 41.

Further, under each of the XY boards 43, 44, XY support boards 43a, 44a to support XY plane movement of the XY boards 43, 44 are provided. The X support board 43a of the X board 43 is integrally constituted with the Y board 44 and the Y axis movement of the Y board 44 is transmitted from the upper surface thereof to the X board 43, thereby The Y axis movement of the X board 43 is prompted.

Next, it will be described the technology to put the filtered fungus on the measurement filter 17a from the specimen after mixing the specimen in the staining solution.

First, the specimen on which the fungus is adhered is dissolved in the physiological saline and it is prepared solution in which such physiological saline and two kinds of the fluorescent dye for live bacteria and dead bacteria are mixed. Concretely, in measurement object, against the specimen 1g which is obtained by using different collection method in each of a case that the specimen on which the fungus is adhered exists within the measurement object and a case that the specimen exists on the surface of the measurement object, the physiological saline 9 cc which is sterilized is added and diluted by stirring.

Next, in solution obtained by separating solid residue of the specimen existing in the solution in which the specimen is dissolved by filtering or centrifuge, fluorescent dye solution for live bacteria and for dead bacteria and dyeing accelerator or spill prevention agent are mixed and dissolved, thereby solution is prepared.

Here, as the fluorescent dye solution, for example, fluorescein for live bacteria or derivatives thereof and propidiumiodide for dead bacteria can be utilized.

Fluorescein is dispersed in the cells of live bacteria and is captured in the cells of dead bacteria and strong fluorescence emission of the center wavelength 530 nm is presented by adsorbing the excitation light of the center wavelength 480 nm.

On the other hand, propidiumiodide cannot penetrate in the cells of live bacteria and can penetrate and disperse in the cells of dead bacteria. Strong fluorescence emission of the center wavelength 620 nm is presented by adsorbing excitation light of the center wavelength 530 nm.

Further, the fluorescent dye made of fluorescein for live bacteria and propidiumiodide for dead bacteria are prepared with concentration at least more than 3 μmol/ml when diluted in physiological saline so as to present fluorescence emission which can be imaged according to adsorption of the excitation light. Here, since there is a danger that excessive concentration gives adverse effect to the live bacteria, it is desirable that concentration is limited to 15 μmol/ml at most.

Furthermore, it may be conceivable that propidiumiodide used for fluorescent staining of the live bacteria is dissolved in dimethylsulfoxide (DMSO) as solvent while expecting staining promotion effect. Although penetration inhibition of the fluorescent dye into the cells mainly causes in cell membrane, DMSO can raise penetration of the fluorescent dye into the fungus cells.

Further, to prevent spill of the fluorescent dye penetrated in the live bacteria and in the dead bacteria, the spill prevention agent may be added. As the spill prevention, for example, potassium chloride solution may be adopted.

Next, solution in which the fungus is dispersed and staining agent is mixed (hereafter, called as staining fungus solution) is heated to room temperature or required temperature if necessary, preferably heated to 25 to 35° C., thereby the fluorescent dye is penetrated in the fungus cells and effective staining is conducted, in addition to operation of the staining promotion agent. Although time necessary for staining is different somewhat according to heating condition, such time is roughly the extent of 3 to 15 minutes.

Figure 4A:
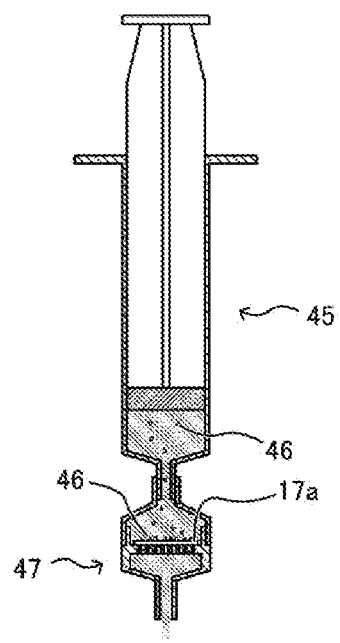
FIGS. 4A-4C are explanatory views showing a filtration step in which fungus stained fluorescently is filtered off on a filter.

Next, as shown in FIG. 4A, the staining fungus solution obtained in the above is injected in a syringe 45 and the staining fungus solution is pumped to a filter cartridge 47 in which the measurement filter 17a is accommodated, thereby the fungus 46 is trapped on the measurement filter 17a.

Figure 4B:
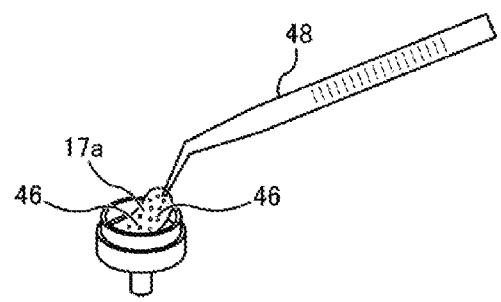

According to this operation, as shown in FIG. 4B, the fungus 46 stained by the fluorescent dye is filtered out on the measurement filter 17a.

Figure 4C:
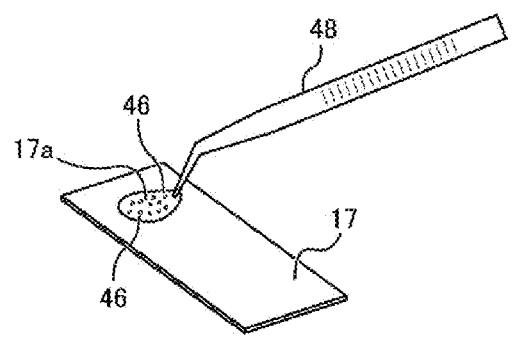

Further, as shown in FIGS. 4B and 4C, the measurement filter 17a on which the fungus 46 is filtered out is put on the fungus base 17 by using a tweezers 48, etc. Thereafter, the live/dead bacterial state is determined by the determination device A.

Next, it will be described in detail a determination process of a measurement sample prepared in the above by the determination device A.

First, as shown in FIG. 1, the opening/closing lid body 12 of the case body 10 is opened and the fungus base 17 on which the measurement filter 17a having the filtered out fungus 46 is put is inserted through the fungus base insertion port 14 and fixed on the fungus base holding mechanism 15.

Figure 5:
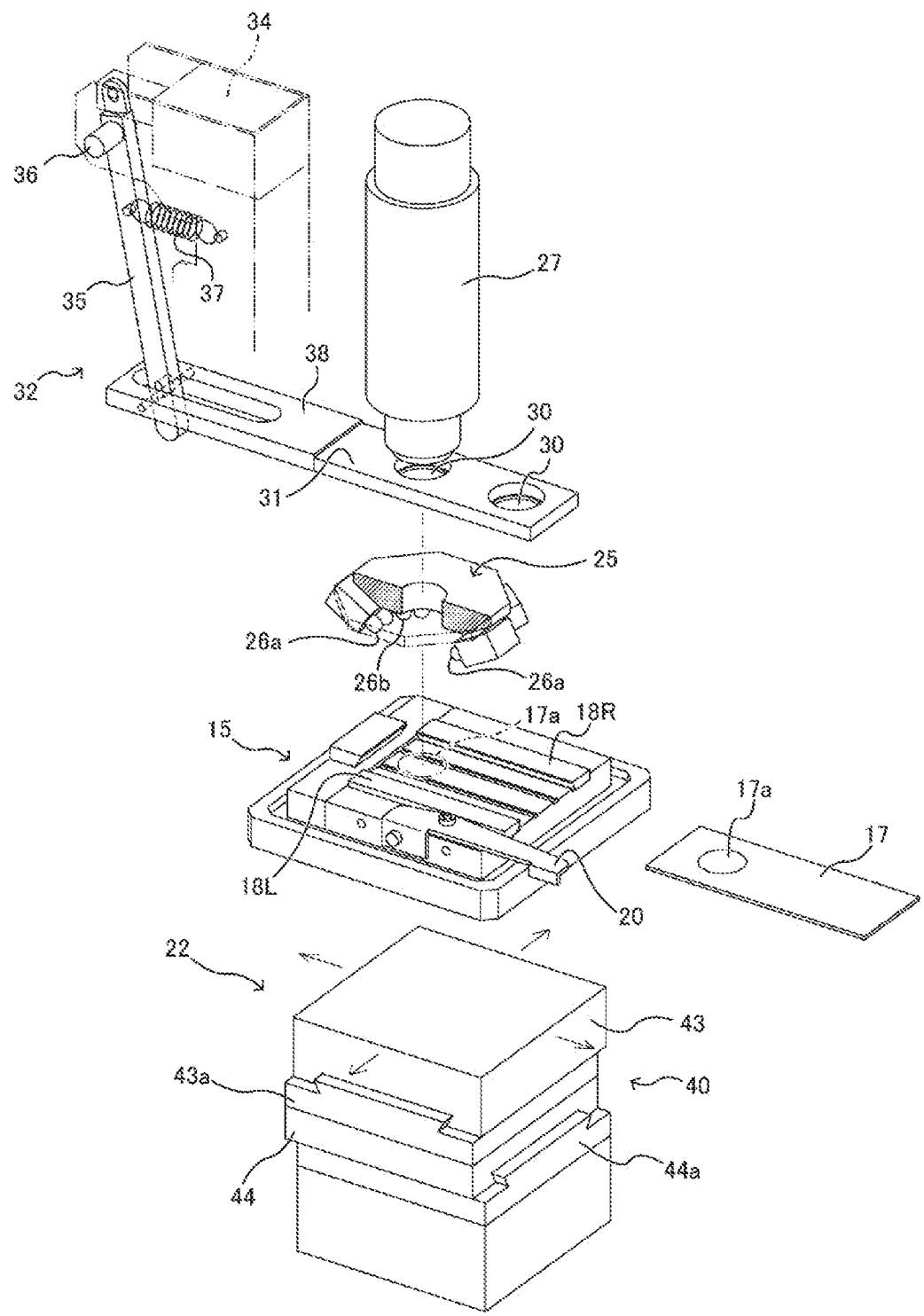
FIG. 5 is an exploded perspective view showing a main part constitution of a measurement mechanism.

Concretely, as shown in FIG. 5, positions of the left and right rails 18L, 18R are displaced by the operation lever 20 through the fungus base insertion port 14, thereby both side edges of the fungus base 17 are clamped by the left and right rails 18L, 18R from the left and right outsides and setting of the fungus base 17 is completed while adjusting to proper measurement position.

Thereafter, the opening/closing lid body 12 of the case body 10 is closed and the measurement mechanism 11 is operated. Further, it is conducted six-way irradiation while switching two kinds of excitation lights of blue light from the LED 26a for live bacteria and green light from the LED 26b for dead bacteria through the excitation light irradiation mechanism 25 arranged in peripheral of the fungus base holding mechanism 15, thereby the luminescence emission from each of the live bacteria and the dead bacteria on the measurement filter 17a is obtained.

Concretely, by the excitation light irradiation of wavelength 488 nm included in the blue light emitted from the LED 26a for live bacteria of the excitation light irradiation mechanism 25, emission of the green fluorescence of longer wavelength 530 nm is obtained from the live bacteria on the measurement filter 17a in the cells of which fluorescein is penetrated, on the other hand, by the excitation light irradiation of wavelength 530 nm included in the green light emitted from the LED 26b for dead bacteria, emission of the red fluorescence of longer wavelength 620 nm is obtained from the dead bacteria in the cells of which propidiumiodide is penetrated.

In the irradiation state of the excitation light mentioned in the above, the band pass filter 30 arranged between the imaging camera 27 and the measurement filter 17a is switched for live bacteria or for dead bacteria through the filter switching mechanism 32, thereby the excitation light or miscellaneous ray is cut off.

That is, based on electrical advance/retreat operation of the switching solenoid 34, the band pass filter 34 is switched, thereby it is prevented unnecessary miscellaneous ray from being contaminated when the live bacteria and the dead bacteria are respectively imaged. Here, switching of the filter for live bacteria and the filter for dead bacteria in the band pass filter 30 is conducted in conjunction with every one shooting by the imaging camera 27 through the control portion 29.

Shooting by the imaging camera 27 is conducted as follows. That is, the adhered fungus 46 of the measurement filter 17a set in the fungus base holding mechanism 15 is virtually divided into 24 frames by the XY stage 22 and is moved in the XY direction through the XY axes adjustment mechanism 40 of the fungus base holding mechanism 15, thereafter shooting by the imaging camera 27 is separately conducted for live bacteria and for dead bacteria through the band pass filter 30 every virtual grid section of each of 24 frames.

That is, in one virtual grid section, every shooting of the live bacterial and the dead bacteria is respectively conducted in one time, movement distance information centering the origin position of the XY axes adjustment mechanism 40 of the fungus base holding mechanism 15 is transmitted to the control portion of each of X axis and Y axis motors 41, 42 (illustration is omitted), thereby correction of the origin position is conducted.

Further, the measurement filter 17a on the XY stage 22 is adjusted and positioned to the other virtual grid section which is the next imaging point, thereby the adhered fungus 46 on the measurement filter 17a is shot in total 24 frames, 24 times respective for live bacteria and for dead bacteria, total 48 times through the imaging camera 27.

Further, concerning images shot by the imaging camera 27, each fluorescent emission strength obtained from the live bacteria and the dead bacteria by irradiation of the excitation light is grasped by the CMOS image sensor 28 (see FIG. 2) and image process thereof is conducted in the control portion 29.

In the image process in the control portion 29, it is roughly conducted grayscale image conversion step, fungus matching pattern step, live bacteria matching number recording step, etc.

Figure 6:
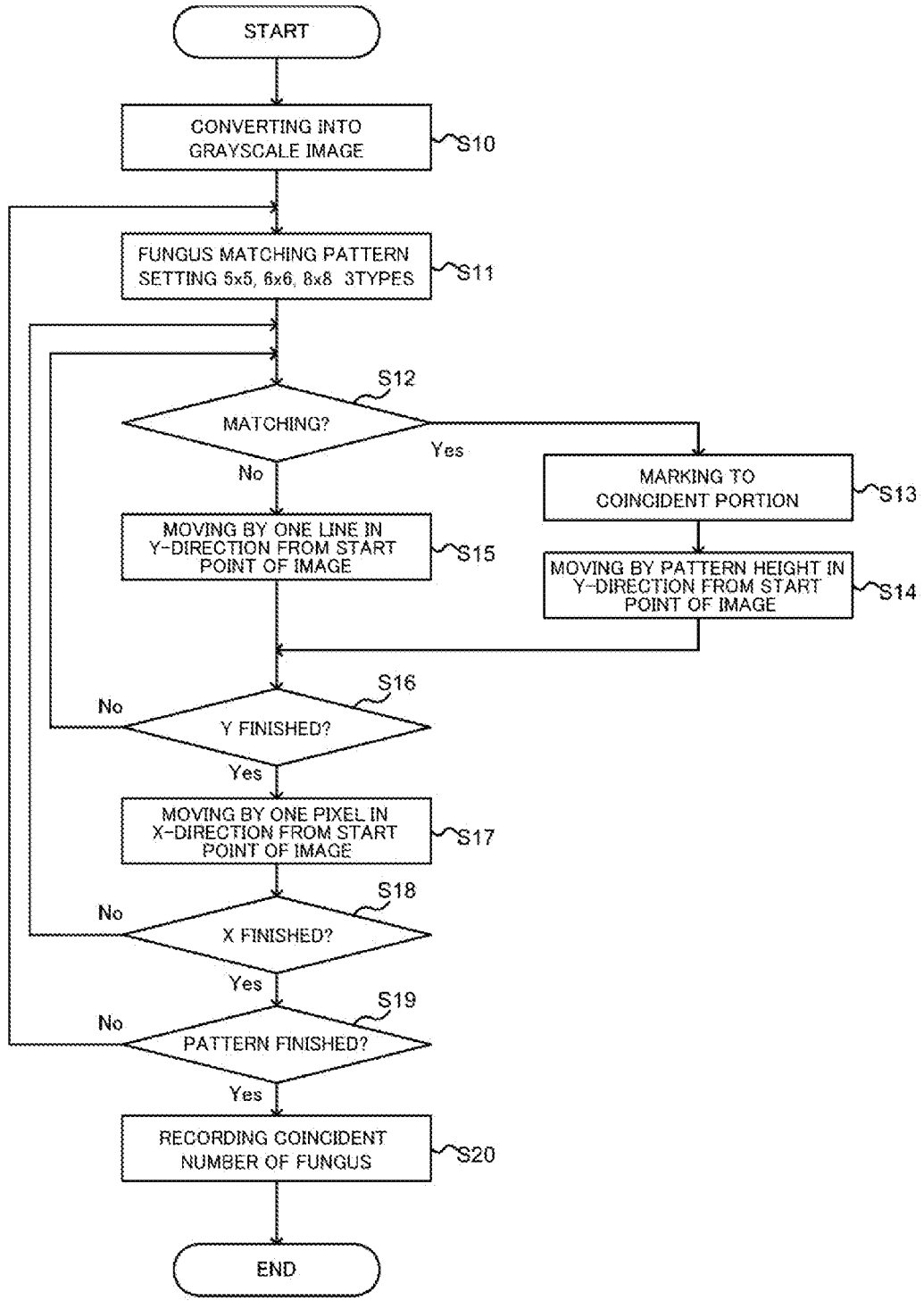
FIG. 6 is a flowchart showing image processes executed in a control portion.

Concretely, as shown in the flowchart of FIG. 6, first, it is conducted the grayscale image conversion step (step S10) in which image data obtained from the CMOS image sensor 28 is converted in grayscale image.

Next, based on information converted in the grayscale image, the fungus matching pattern step to determine the fungus is conducted.

The fungus matching pattern step is conducted by verifying coincidence of specific shape patterns of fungus species recorded beforehand in the control portion 29 and shapes of subjects represented on the grayscale images for each of image data of the live bacteria and the dead bacteria.

Further, as for setting of this fungus matching pattern, there are three kinds of setting in which pixel number of XY axes is 5×5. 6×6 and 8×8 (step S11) for the specific shape pattern of the recorded fungus species and following operation is repeatedly conducted every setting.

Verification of the specific shape pattern of the fungus species recorded in the control portion 29 and the object shape represented on the grayscale image is conducted by scanning verification to move the specific shape pattern in the Y axis direction every one pixel from an image start point within the virtual grid section of one frame on the gray scale image (step S12, step S15).

At that time, in a case that a point coinciding with the specific shape of the fungus species recorded in the control portion 29 is discovered on the grayscale image (step S12: Yes), a spot mark is attached to the coincided spot (step S13). After marking, the specific shape pattern is moved and adjusted by amount corresponding to the specific shape pattern already marked from the scanning start point of the image (step S14) and continuation of the scanning verification is started (step S16: No).

In a case that the scanning verification for one row, that is, longitudinal one row is completed (step S16: Yes), the specific shape pattern is moved by one pixel in the X-axis direction from the scanning start point of the image, that is, moved in the lateral direction (step S17), and the scanning verification is conducted in the longitudinal direction (step S18: No).

As mentioned, the scanning verification is conducted over the longitudinal and lateral within all areas of the virtual grid section of one frame on the grayscale image and it is conducted identification operation for 24 frames in which marking is done for each of the live bacteria and the dead bacteria (step S19).

Further, in the live bacteria matching number recording step, a number of spot marked every live bacteria and the dead bacteria within each virtual grid section is recognized as identification number for each of live bacteria and dead bacteria and recorded every virtual grid section (step S20).

The above determined information of number of the live bacteria and the dead bacteria existing on the measurement filter is reflected on a monitor of the computer C together with the image data obtained by the imaging camera 27, thereby the state of the fungus can be grasped as the image and the live/dead bacterial state can be determined.

On the other hand, on the computer C, each image data obtained in the above is displayed and the information of number of the live bacteria and the dead bacteria detected in each image data is also displayed together with the image data.

As mentioned, according to the determination device A of the present embodiment, it is not necessary to count the live bacteria and the dead bacteria one by one while the user conducts speculum with the naked eye and has a counter at one hand. In spite of comparative easy operation, the fungus state can be accurately grasped in comparison with the conventional operation. Further, the fungus state of the live bacteria and the dead bacteria can be accurately grasped through the images shot in the above. That is, it can be provided a microorganism fluorescence image measurement device or a microorganism fluorescence image measurement method, both possessing above constitution.

Next, it will be described a live bacteria/dead bacterial state determination device according to the first modification (hereafter, called as the determination device A2). Here, in each modification described hereinafter, as for the constitution almost as same as that of the mentioned determination device A, there will be a case that explanation thereof is omitted. And as for the constitution of each modification described hereafter, for example, electrical constitution and the like, it can be understood that such constitution is also provided in the above determination device A, conversely, it can be also understood that the constitution in the above determination device A is provided in each modification described hereinafter.

The determination device A2 is characterized in a point that the device is constituted so that the number of the fungus can be more accurately counted. In the determination device A described above, light quantity of the excitation light irradiated from the LED 26a for live bacteria or the LED 26b for dead bacteria is not particularly adjusted and, for example, in a case that light quantity of the excitation light irradiated from these LEDs 26 is made constant, emission quantity of the fluorescence from entire of the fungus increases when the fungus 46 per a predetermined area on the measurement filter 17a is large, therefore a border of an outer periphery of some one fungus 46 and an outer periphery of another fungus 46 close to the former becomes ambiguous on the obtained image. Thus, in spite that two fungi 46 exist, such two fungi 46 are photographed as one light mass on the image, therefore recognition of each fungus 46 by the pattern matching, that is, it becomes difficult to separately recognize individual fungus 46, thus, there will be considered a case that calculation of accurate number of fungus becomes difficult.

Further, in a case that the number of the fungus per a predetermined area on the measurement filter 17a is small, emission quantity of fluorescence from entire of the fungus decreases, thus it is considered a problem that possibility to falsely recognize fluorescence noise emitted from contaminants fluorescent stained as the fungus 46 is raised.

Thus, in the determination device A2, when shooting on the measurement filter 17a is conducted, approximate value of the number of the fungus is obtained from the first frame (shooting of the first grid section) becoming the standard. Thereafter, in a case that the obtained value of the number of the fungus is more than a predetermined value, light quantity of the excitation light emitted from the LED 26 is reduced, thus the border of each fungus 46 is made clear by suppressing emission quantity of fluorescence. Further, in a case that the obtained value of the number of the fungus is less than the predetermined value, emission quantity of fluorescence is increased by increasing light quantity of the excitation light, thus the fungus shape can be imaged more clearly. Thereby, accurate measurement of the number of the fungus can be conducted.

Hereinafter, first the electrical constitution of the determination device A2 will be described, thereafter processes in the control portion 29 will be described.

Figures 7, 8:
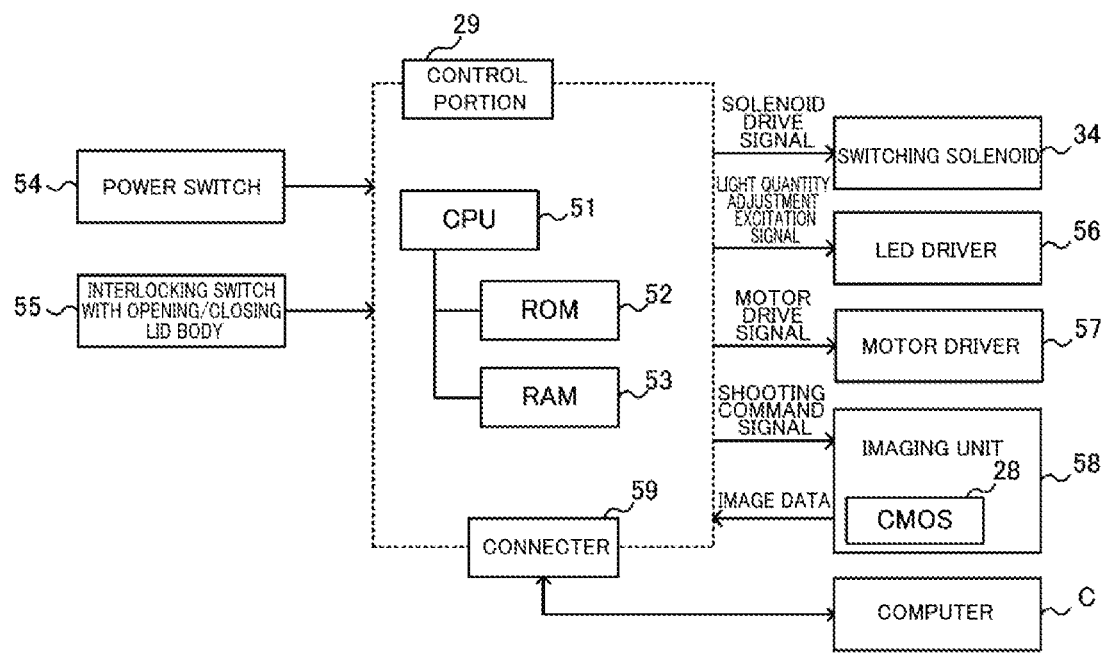
FIG. 7 is a block diagram showing a main electrical constitution.
FIG. 8 is an explanatory view showing a light quantity table.

FIG. 7 is a block diagram showing main electrical constitution in the determination device A2. As shown in FIG. 7, the control portion 29 possesses a CPU 51, a ROM 52 and a RAM 53. In the ROM 52, programs necessary for processes of the CPU 51 are stored and the RAM 53 functions as a temporary storing area when the programs, etc. are executed.

Concretely, in the RAM 53, image data shot by the CMOS image sensor 28, a count value of the number of the fungus and shooting flags of the dead bacteria, etc. are stored. The count value of the number of the fungus is a number of the fungus detected by conducting the pattern matching process through the CPU 51 and both a count value of the number of the live bacteria and a count value of the number of the dead bacteria are stored. Further, the shooting flag of the dead bacteria is a flag utilized for determination whether a timing to shoot the dead bacteria becomes or not. In a case that the timing to shoot the dead bacteria does not become (for example, the timing to shoot the live bacteria becomes), the shooting flag is set to OFF and in case that the timing to shoot the dead bacteria becomes, the shooting flag is set to ON.

In the ROM 52, programs to realize various processes necessary to operate the determination device A2, template images necessary for the pattern matching, tables referred when determination is conducted by the CPU 51 are respectively stored in predetermined areas. For example, as the tables, as shown in FIG. 8, it is stored a light quantity table to change light quantity of the excitation light from the LED 26 corresponding to the number of the fungus, etc. That is, this light quantity table is a table in which the number of the fungus detected by the pattern matching and processes for a LED driver 56 described hereafter are mutually corresponded.

Further, to the control portion 29, as shown in FIGS. 1 and 2, a power switch 54 and an interlock switch 55 interlocked with the opening/closing lid body are connected. The power switch 54 functions as a main switch to operate the determination device A2 and the interlock switch 55 is a switch to detect whether the opening/closing lid body 12 is in an opened state or a closed state.

Further, to the control portion 29, the switching solenoid 34, a LED driver 56, a motor driver 57 and an imaging unit 58 are connected.

The control portion 29 transmits a solenoid drive signal including information of timing to shoot which of the live bacteria or the dead bacteria to the switching solenoid 34. The switching solenoid 34 receiving the solenoid drive signal drives itself corresponding to signal content and operates the filter switching mechanism 32, thereby switches band pass filter 30.

The LED driver 56 possesses a circuit to switch turning on of the LED 26a for live bacteria or the LED 26b for dead bacteria and to conduct light quantity adjustment of each LED 26 and operates corresponding to an excitation signal or a light quantity adjustment signal transmitted from the control portion 29.

Further, the LED driver 56 possesses a storing area in which it is stored an emission reference value for live bacteria and an emission reference value for dead bacteria (collectively called as emission reference value) which are referred at the time of light quantity adjustment when the LED 26a for live bacteria or the LED 26b for dead bacteria is emitted. As the emission reference value, there are stored as expected values the values corresponding to excitation light quantity of the LED 26 from which moderate fluorescence is obtained in a case that appropriate number of fungus exist.

In the excitation signal, information to instruct turning on of the LED 26a for live bacteria (hereinafter, excitation signal including this information is called as excitation signal for live bacteria) to the LED driver 56 or information to instruct turning on of the LED 26b for dead bacteria (hereafter, excitation signal including this information is called as excitation signal for dead bacteria) to the LED driver 56 are included.

In a case that the LED driver 56 receives the excitation signal, for example, the excitation signal for live bacteria, the LED driver 56 emits the LED 26a for live bacteria with strength corresponding to the emission reference value for live bacteria and, in a case that the LED driver 56 receives the excitation signal for dead bacteria, the LED driver 56 emits the LED 26b for dead bacteria with strength corresponding to the emission reference value for dead bacteria.

Further, in the light quantity adjustment signal, dimming information to instruct dimming to the LED driver 56 (hereinafter, light quantity adjustment signal including dimming information is also called as dimming signal) or boosting information to instruct boosting to the LED driver (hereinafter, the light quantity adjustment signal including the boosting information is also called as boosting signal) or information that the LED 26 to be dimmed or boosted is which of the LED 26a for live bacteria or the LED 26b for dead bacteria, are included.

In a case that the LED driver 56 receives the light quantity adjustment signal, for example, the dimming signal concerning the LED 26a for live bacteria, the LED driver 56 rewrites the emission reference value for live bacteria so that the emission strength of the LED 26a for live bacteria becomes low, and in a case that the LED driver 56 receives the boosting signal concerning the LED 26b for dead bacteria, the LED driver 56 rewrites the emission reference value for dead bacteria so that the emission strength of the LED 26b for dead bacteria becomes high.

The motor driver 57 is a circuit portion conducting drive control of the X axis motor 41 and the Y-axis motor 42. The control portion 29 outputs a motor drive signal to the motor driver 57. The motor driver 57 receiving the motor drive signal moves the XY stage 22 so that a predetermined shooting range (grid section) enters within the shooting grid section according to a coordinate stored beforehand.

The imaging unit 58 possesses the CMOS image sensor 28, constructs image data from a signal obtained by the CMOS image sensor 28 and transmits the image data to the control portion 29. When the control portion 29 transmits an imaging command signal to the imaging unit 58, the imaging unit 58 returns the image data obtained by imaging to the control portion 29.

Further, the control portion 29 possesses a connector and can conduct bidirectional communication with the computer C through the connector 59.

Next, referring to FIG. 9, it will be described a count process for live bacteria/dead bacteria on the measurement filter 17a (hereinafter, called as count process for live bacteria/dead bacteria) executed in the control portion 29. The count process for live bacteria/dead bacteria executed in the control portion 29 is executed as a part of general process supervising the determination device A2 (hereinafter called as main routine). Here, the count process for live bacteria/dead bacteria will be concretely described and the other various processes in the main routine will be omitted.

Figure 9:
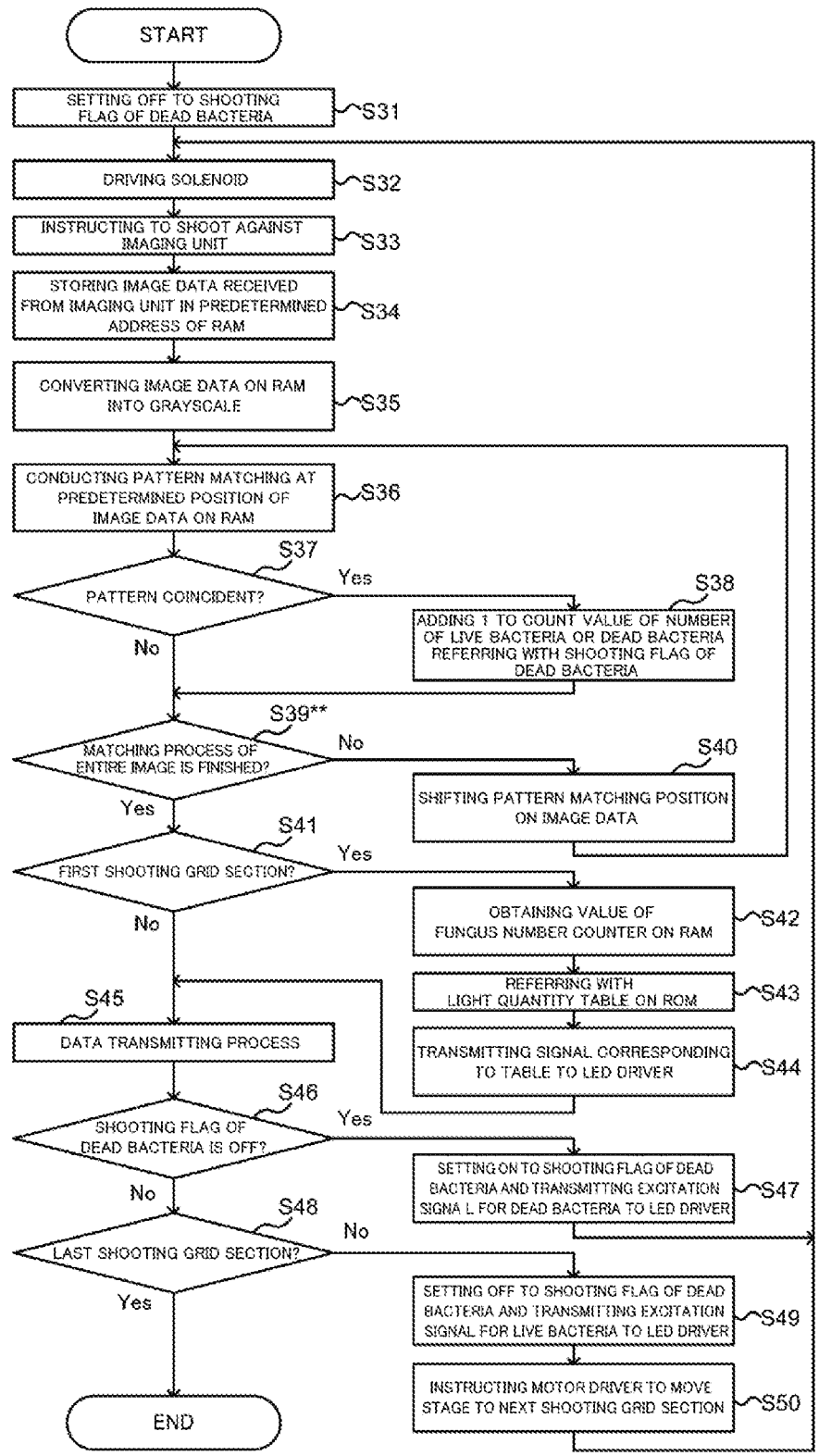
FIG. 9 is a flowchart showing processes executed in the control portion.

As shown in FIG. 9, in the count process for live bacteria/dead bacteria, first the CPU 51 rewrites the value of the imaging flag for dead bacteria stored in a predetermined address of the RAM 53 and sets OFF thereto (step S31). Further, the CPU 51 transmits the excitation signal for live bacteria to the LED driver 56.

Next, the CPU 51 transmits the solenoid drive signal to the switching solenoid 34 with reference to the shooting flag for dead bacteria, thereby switches the band pass filter (step S32). That is, in a case that the shooting flag for dead bacteria is OFF, the CPU 51 transmits the solenoid drive signal including information that it is the timing to shoot the live bacteria and arranges the band pass filter 30 between the measurement filter 17a and the imaging camera 27. In a case that the shooting flag for dead bacteria is ON, the CPU 51 transmits the solenoid drive signal including information that it is the timing to shoot the dead bacteria and arranges the band pass filter 30 for dead bacteria.

Next, the CPU 51 transmits the shooting command signal to the imaging unit 58 and makes the imaging camera 27 conduct shooting (step S33), stores the image data received from the imaging unit 58 in a predetermined address of the RAM 53 (step S34) and converts the image data into greyscale (step S35).

Next, the CPU 51 conducts the pattern matching while referring the template image stored in the ROM 52 at the predetermined position on the image data stored in the RAM 53 (step S36). The pattern matching method done here may be the method described in the above determination device A and it can be adopted a well-known method.

Next, the CPU 51 determines whether or not the pattern matching conducted at the predetermined position of the image data coincides with the template image (step S37). Here, as for coincidence with the template image, it is not necessary to completely coincide with the template image, thus it also includes a state included within a certain allowable range such as luminance, size, shape, etc.

Here, when it is determined that the pattern matching coincides with the template image (step S37: Yes), the CPU 51 refers the shooting flag for dead bacteria, and when the shooting flag for dead bacteria is OFF, the CPU 51 adds 1 to the count value of the number of the live bacteria, and when the shooting flag for dead bacteria is ON, the CPU 51 adds 1 to the count value of the number of the dead bacteria (step S38).

On the other hand, when it is determined that the pattern matching does not coincide with the template image (step S37: No), the CPU 51 determines whether or not the pattern matching process of the entire image stored in the RAM 53 is finished (step S39). Here, when it is determined that the pattern matching is not finished (step S39: No), the CPU 51 shifts the pattern matching position on the image data (Step S40) and return the procedure to S36.

On the other hand, when it is determined that the pattern matching process is finished (Step S39: Yes), the CPU 51 determines whether the pattern matching is the first shooting grid section or not (step S41).

Here, when it is determined that the pattern matching is not the first shooting grid section (Step S41: No), the CPU 51 returns the procedure to step S45. On the other hand, when it is determined that the pattern matching is the first shooting grid section (step S41: Yes), the CPU 51 obtains the count value of the number of the fungus on the RAM 53 while referring the shooting flag for dead bacteria (step S42). Concretely, the CPU 51 obtains the count value of the number of the live bacteria when the shooting flag for dead bacteria is OFF and obtains the count value of the number of the dead bacteria when the shooting flag for dead bacteria is ON.

Next, the CPU 51 determines the fungus amount with reference to the light quantity table stored in the ROM 52 (step S43) and transmits to the LED driver 56 the light quantity adjustment signal corresponding to the table. (step S44). And at that time, the CPU 51 produces the light quantity adjustment signal including information that the LED 26 to be dimmed or boosted is which of the LED 26a for live bacteria or the LED 26b for dead bacteria corresponding to the state of the shooting flag for dead bacteria. In the present modification, the fungus amount is determined as "large" when the fungi approach within the shooting grid section, thereby the fungus amount is more than the number of the fungus that false detection is raised, and the fungus amount is determined as "moderate" when the fungus amount is appropriate, and the fungus amount is determined as "small" when the fungus amount is less than the number of the fungus that S/N ratio deteriorates. However, it is not necessary to determine by three stages, thus it may be of course good to subdivide in more stages. And for example, when determined as "large", the CPU 51 transmits the dimming signal to the LED driver 56 and when determined as "small", the CPU 51 transmits the boosting signal.

Next, the CPU 51 conducts data transmission process to transmit data such as the image data stored in the RAM 53, the count value for live bacteria, the count value for dead bacteria, etc. to the computer C through the connector 59 (step S45).

Next the CPU 51 determines whether the value of the shooting flag for dead bacteria is OFF or not (step S46). Here, when it is determined that the value of the shooting flag for dead bacteria is OFF (Step S46: Yes), the CPU 51 rewrites the value of the shooting flag for dead bacteria stored in the RAM 53 into ON and transmits the excitation signal for dead bacteria to the LED driver 56 (step S47) and returns the procedure to S32.

On the other hand, when it is determined in step S46 that the shooting flag for dead bacteria is not OFF (step S46: No), the CPU 51 determines whether the pattern matching is the last shooting grid section or not (step S48). Here, when it is determined that the pattern matching is the last shooting grid section (step S48: Yes), the CPU 51 finishes the procedure and returns the procedure to the main routine if necessary.

On the other hand, in the step S48, when it is determined that the pattern matching is not the last shooting grid section (step S48: No), the CPU 51 rewrites the value of the shooting flag for dead bacteria stored in the RAM 53 into OFF and transmits the excitation signal for live bacteria to the LED driver 56 (step S49). Further, the CPU 51 transmits motor drive signal to the motor driver 57 and moves the XY stage 22 to the next shooting grid section (step S50) and returns the procedure to S32.

Therefore, according to the determination device A2 of the present first modification possessing the above constitution, in the first shooting grid section, first, in a case that appropriate amount of the fungus exists, approximate value of the number of the fungus is obtained by the excitation light quantity of the LED 26 from which appropriate fluorescence can be obtained and when the obtained value of the number of the fungus is larger than the predetermined value, light quantity of the excitation light is reduced and emission quantity of fluorescence is suppressed, thereby the border of each fungus can be made clear and accurate measurement of the number of the fungus can be conducted.

Further, when the obtained value of the number of the fungus is smaller than the predetermined value, light quantity of the excitation light is increased, thereby emission quantity of fluorescence is increased and the fungus shape can be imaged more clearly, therefore accurate measurement of the number of the fungus can be conducted.

Next, with reference to FIGS. 10 and 11, it will be described a determination device for determining a live/dead bacterial state according to the second modification (hereinafter, called as determination device A3).

Similar to the determination device A2, although the determination device A3 has also a characteristic that the determination device A3 is constituted so as to be able to more accurately count the number of the fungus, the determination device A3 has a different constitution at a point that light quantity of excitation light is especially adjusted corresponding to an extent of staining of the fungus. Among fungi to be measured, there exist fungus to be easily stained and fungus difficult to be stained, depending on the type of the fungus. This concludes: when the light quantity of the excitation light (LED light) is made constant, in spite that irradiation quantity of the excitation light is same, there will exist the fungus with sufficient fluorescence emission and the fungus with insufficient fluorescence emission. In particular, as for the fungus with insufficient fluorescence emission, such fungus will not be object for the pattern matching, will lead to missing count, therefore there will be a case that accurate count of the number of the fungus becomes difficult.

Thus, in the determination device A3, when shooting on the measurement filter 17a is conducted, it is conducted the pattern matching process of the image data obtained in the first frame (shooting of the first grid section) which becomes the standard, luminance is calculated for a plurality of light spots recognized as the fungus through the pattern matching, an average value of luminance of the plural light spots is obtained, emission quantity of fluorescence is increased by increasing light quantity of the excitation light when the obtained average value of the luminance is smaller than the predetermined value, thereby the fungus shape can be more clearly image and the number of the fungus can be more accurately measured.

Concrete constitution of the determination device A3 is approximately as same as the determination device A and the determination device A2, thus most explanation entrusts the previous explanation. Describing characteristic difference, first in the predetermined storing area of the ROM 52 provided in the control portion 29, it is stored a light quantity table in which luminance shown in FIG. 10 and process to the LED driver 56 are corresponded.

Figures 10, 11:
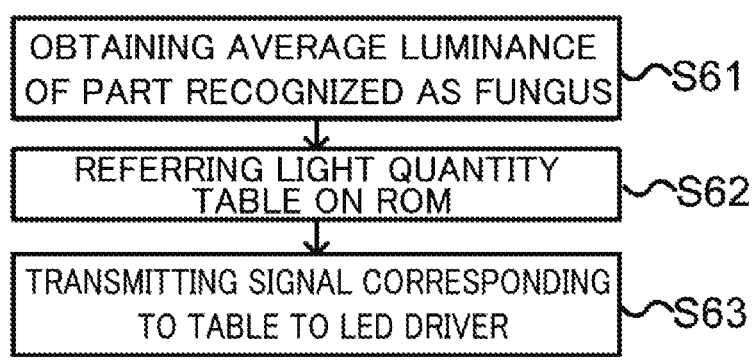
FIG. 10 is an explanatory view showing a light quantity table.
FIG. 11 is a flowchart showing processes executed in the control portion.

Further, in place of step S42~step S44 in the flowchart shown in FIG. 9, step S61~step S63 shown in FIG. 11 will be executed.

Therefore, the control portion 29 starts processes according to the flowchart shown in FIGS. 9 and 11, instructs to shoot against the imaging unit 58 after setting the band pass filter 30 for live bacteria (step S31~step S33), stores the image data received from the imaging unit 58 in the RAM 53 and converts the image data into the greyscale (step S34~step S35) and conducts the pattern matching process over the entire image data and counts the number of the live bacteria (step S36~step S40).

Next, when the shooting grid section is the first shooting grid section (Step S41: Yes), as shown in FIG. 11, the CPU 51 calculates the average value of the luminance from the luminance of a plurality of parts on the image data recognized as the fungus through the pattern matching process (step 61).

Next, the CPU 51 determines the luminance with reference to the light quantity table stored in the ROM 52, that is, the table shown in FIG. 10 (step S62) and transmits the light quantity adjustment signal corresponding to the table to the LED driver 56 (step S63). For example, when it is determined that many fungi comparatively difficult to be stained are detected, it is determined as low luminance, thus it leads that the boosting signal is transmitted to the LED driver 56. In the present modification, as for luminance determination, it is determined as "low luminance" when the average value of luminance of the light spot determined as the fungus in the shooting grid section is less than the luminance of the extent that fear of detection leakage increases. When the average value is appropriate luminance, it is determined as "medium luminance", and when the average value is high luminance of extent that fear deviating from the pattern matching increases, it is determined as "high luminance". However, it is not necessary to determine by three stages and it may be, of course, good to subdivide stages.

Further, after the data transmission process to the computer is done (step S45), the above described similar process is again conducted for the image data obtained through the shooting of the fungus of the dead bacteria (step S46: Yes) and the number of the fungus is calculated by the pattern matching process while shooting with the adjusted luminance for the shooting grid section subsequent to the second shooting grid section.

As mentioned, according to the determination device A3, the luminance is measured for a plurality of light spots on the image recognized as the fungus through the pattern matching in the first frame which becomes the standard and the average value of luminance is obtained, emission quantity of fluorescence is increased by increasing light quantity of the excitation light when the obtained average value of the luminance is smaller than the predetermined value, thereby the fungus shape can be more clearly imaged and the number of the fungus can be more accurately measured.

Next, with reference to FIGS. 12 and 13, it will be described a determination device for determining a live/dead bacterial state according to the third modification (hereinafter, called as determination device A4).

Similar to the determination devices A2 and A3, although the determination device A4 has also a characteristic that the determination device A4 is constituted so as to be able to more accurately count the number of the fungus, the determination device A4 has a different constitution at a point that a process is conducted so that accurate count of the number of the fungus can be done as much as possible in a case that many fungi exist in the shooting grid section and most of these fungi are fungi difficult to be fluorescent stained.

In other words, the determination device A4 is s determination device possessing the feature point of the determination device A2 and A3, and when many fungi difficult to be stained are detected, the determination device A4 dares to reduce the excitation light quantity and conducts a plurality of shootings for each of the live bacteria and the dead bacteria concerning one shooting grid section, thereby the determination device A4 solves two problems one of which is a problem concerning separate detection of two fungi adjacent with each other and the other of which is a problem concerning S/N ratio.

Concretely, first in the predetermined storing area of the ROM 52 provided in the control portion 29, it is stored a light quantity table in which, as shown in FIG. 12, the luminance and the number of the fungus, process to the LED driver 56 are mutually corresponded.

Further, in place of step S42~step S44 in the flowchart shown in FIG. 9, step S71~step S74 shown in FIG. 13 are executed.

Further, in the predetermined address of the RAM 53, a multiple shooting flag indicating whether multiple shootings are to be conducted or not is assigned. This multiple shooting flag takes two values of ON or OFF and an initial value thereof is set to OFF.

Therefore, when the control portion 29 of the determination device A4 starts processes according to the flowchart shown in FIGS. 9 and 13, the control portion 29 makes the shooting flag for dead bacteria OFF and the multiple shooting flag OFF (step S31) and after setting the band pass filter 30 for shooting the live bacteria, the control portion 29 transmits the shooting command signal including the state of the multiple shooting flag to the imaging unit 58 and instructs to shoot (step S32~step S33), stores the image data received from the imaging unit 58 in the RAM 53 and converts the image data into the greyscale (step S34~step S35) and conducts the pattern matching process over the entire image data and counts the number of the live bacteria (step S36~step S40).

Next, when the shooting grid section is the first shooting grid section (step S41: Yes), as shown in FIG. 13, the CPU 51 obtains the count value of the number of the fungus on the RAM 53 after referring the shooting flag for dead bacteria (step S71). Here, since the shooting flag for dead bacteria is OFF, the count value for live bacteria is obtained. Next, the CPU 51 calculates the luminance average value from the luminance of a plurality of parts on the image data recognized as the fungus by the pattern matching process (step S72).

Next, the CPU 51 determines the number of fungus and the luminance with reference to the light quantity table stored in the ROM 52, that is, the table shown in FIG. 12 (step S73) and transmits the light quantity adjustment signal corresponding to the table to the LED driver 56 (step S74). For example, when the detected number of the fungus is many and the average luminance of these fungi is a luminance of extent that fear of detection leakage increases, it is determined as "low luminance" and "many fungi" and it is transmitted the dimming signal to the LED driver 56 and the multiple shooting flag is made ON. It may be. Of course, good to subdivide the determination of luminance and the number of the fungus in the present modification, as described in the above determination device A2 and the determination device A3.

Further, after the data transmission process to the computer is finished (step S45), the process similar to the above process is again conducted for the image data obtained by the shooting of the dead bacteria (step S46: Yes). After the count process, etc. of the dead bacteria in the first shooting grid section is finished, processes for the shooting grid sections subsequent to the second shooting grid section are started (step S48: No~step S50→step S32).

Here, when it is conducted the shooting for the shooting grid section subsequent to the second shooting grid section, the CPU 51 transmits the shooting command signal including information of the value of the multiple shooting flag, that is, the multiple shooting flag=ON to the imaging unit 58 and instructs to shoot.

The imaging unit 58 receiving the information of the multiple shooting flag=ON conducts shooting of predetermined multiple sheets (for example, 2~10 sheets) at the same position and transmits these image data to the control portion 29.

In the control portion 29 receiving the image data of plural sheets, the CPU 51 converts each image data into the greyscale, thereafter the CPU 51 produces one luminance averaged image data in which the luminance at the predetermined position over the entire shooting range is made as the average luminance among image data (step S35).

Further, the pattern matching process is done against the obtained luminance averaged image data, thereby count of the number of the fungus is conducted.

As mentioned, according to the determination device A4, luminance is measured for a plurality of light spots recognized as the fungus through the pattern matching in the first frame which becomes the standard and the average value of the luminance is obtained and approximate value of the number of the fungus is obtained, light quantity of the excitation light is adjusted when the shooting is conducted for the shooting grid section subsequent to the second shooting grid section corresponding to the obtained luminance and the number of the fungus.

In particular, when the obtained average value of the luminance is smaller than the predetermined value and the number of the detected fungus exists many, the light quantity of the excitation light is reduced and the pattern matching process is done in the shooting grid section subsequent to the second shooting grid section based on the luminance averaged image data obtained by shooting multiple sheets. Thereby, the outline of the fungus can be made more clearly by reducing the light quantity and random noise, etc. getting in the way for the pattern matching can be diluted by producing the luminance averaged image data, thereby the number of the fungus can be more accurately measured.

As mentioned above, according to the determination devices A~A4, such device comprises: a case body inside of which is made a darkroom space in which a measurement mechanism is housed; an opening/closing lid body openable and closable a fungus base insertion port formed in front of the case body; wherein the measurement mechanism is housed in the case body and configured to determine the live bacteria or the dead bacteria of the fungus collected from a specimen and to measure a number of bacteria, and wherein the measurement mechanism comprises: a fungus base holding mechanism that a fungus base on which the fungus collected from the specimen is placed is inserted and fixed; an excitation light irradiation mechanism constituted in capable of intensively irradiating toward the fungus on the fungus base; an imaging camera arranged above the fungus on the fungus base through a fixation frame; and an XY-axes adjustment mechanism for minutely adjusting an XY stage supporting the fungus base holding mechanism and constituted in two separately moving layers in an XY-axes direction. Therefore, it is not necessary to count the live bacteria and the dead bacteria one by one while the user conducts speculum with the naked eye and has a counter at one hand. In spite of comparative easy operation, the fungus state can be accurately grasped in comparison with the conventional operation. Further, the fungus state of the live bacteria and the dead bacteria can be accurately done through the images shot in the above.

The invention claimed is:

1. A determination device for determining a live/dead bacterial state of a fungus comprising:
   a case body inside of which is a darkroom space;
   an opening/closing lid body which opens and closes a fungus base insertion port formed in front of the—case body;
   a measurement mechanism housed in the case body and configured to determine a live bacterial state and a dead bacterial state of a fungus collected from a specimen and to measure a number of fungus;
   wherein the measurement mechanism comprises:
   a fungus base holding mechanism that holds a fungus base on which the fungus collected from the specimen is placed;
   an excitation light irradiation mechanism arranged above the fungus base holding mechanism and capable of irradiating light toward the fungus on the fungus base;
   an imaging camera arranged above the fungus on the fungus base through a fixation frame; and
   an XY-axes adjustment mechanism for moving and adjusting an XY stage having two separately moving layers and supporting the fungus base holding mechanism in an XY-axes direction, wherein the excitation light irradiation mechanism has a plurality of LEDs arranged in a ring and capable of irradiating the fungus with excitation light from diagonally above the fungus to excite a fluorescent substance which was used to dye the fungus, the plurality of LEDs divided into LEDs for irradiating the fungus to detect a live bacterial state and LEDs for irradiating the fungus to detect a dead bacterial state, and the imaging camera is directed to the fungus base through an inner space of the ring of LEDs, wherein the measurement mechanism further comprises a control portion and an optical system through which a measurement filter arranged on the fungus base on which the fungus is adhered is virtually sectioned and the fungus is magnified so as to be able to image the fungus with an angle of view of the imaging camera for every virtual section, and wherein the control portion controls the XY-axes adjustment mechanism so that after the imaging camera images one virtual section, another virtual section enters the angle of view.

2. The determination device for determining a live/dead bacterial state of a fungus according to claim 1,
wherein a filter switching mechanism for switching a plurality of band pass filters is arranged behind the fixation frame of the imaging camera and the plurality of band pass filters are arranged between the fungus base and the imaging camera.

3. The determination device for determining a live/dead bacterial state of a fungus according to claim 1,
wherein the fungus base holding mechanism comprises:
left and right rails for clamping both side edges of the fungus base from left and right outer side directions;
a rail displacement mechanism for releasing the clamping of the fungus base by the left and right rails through displacing one of the left and right rails toward outside; and
an operation lever arranged outside of the one of the left and right rails to operate the rail displacement mechanism from the fungus base insertion port and the operation lever rotationally operate around a support positioned midway of the operation lever;
wherein the rail displacement mechanism comprises:
a slide shaft horizontally projected on the one of the left and right rails;
an operation lever contact projection formed on a head portion of the slide shaft;
an operation support portion supporting a midway portion of the operation lever, a top portion of the operation lever contacts the operation lever contact projection on the XY stage; and
a compression spring provided between an outer side surface of the one of the left and right rails and the top portion of the operation lever.

4. The determination device for determining a live/dead bacterial state of a fungus according to claim 1,
wherein the imaging camera distinguishes the fungus on the measurement filter into a predetermined number of grid sections and an image process is conducted by a computer through light obtained by a CMOS image sensor for every one of the grid sections.

5. The determination device for determining a live/dead bacterial state of a fungus according to claim 1,
wherein the XY-axes adjustment mechanism has an output shaft for an X axis motor and an output shaft for a Y axis motor and the output shaft for the X axis motor and the output shaft for the Y axis motor are interlocked and concatenated to the XY stage, and
wherein an origin position is set on the XY stage beforehand and movement distance information centering the origin position is transmitted to the control portion of each of the X axis motor and the Y axis motor and correction of the origin position is conducted when the XY stage is moved and adjusted in the XY-axes direction.

6. The determination device for determining a live/dead bacterial state of a fungus according to claim 1,
wherein the control portion obtains a value of a number of fungus existing within a first virtual section based on an image data obtained by imaging the first virtual section through the imaging camera,
wherein when the value of the number of fungus is more than a predetermined numerical value, light intensity of excitation light emitted from the LEDs is decreased, and emission intensity of fluorescence from the fungus is suppressed; and
wherein when the value of the number of fungus is less than the predetermined numerical range, light intensity of excitation light emitted from the LEDs is increased, and the emission intensity of florescence from the fungus is increased.

7. The determination device for determining a live/dead bacterial state of a fungus according to claim 1,
wherein the control portion obtains an average value of luminance of light spots for a plurality of fungus existing within a first virtual section based on image data obtained by imaging the first virtual section through the imaging camera,
wherein when the average value of luminance is more than a predetermined numerical value, light intensity of excitation light emitted from the LEDs is decreased, and emission intensity of florescence from the fungus is suppressed, and
wherein when the average value of luminance is less than the predetermined numerical value, light intensity of excitation light emitted from the LEDs is increased, and emission intensity of florescence from the fungus is increased.

8. The determination device for determining a live/dead bacterial state of a fungus according to claim 1,
wherein the control portion obtains a value of a number of fungus existing within a first virtual section and obtains an average value of luminance of light spots for a plurality of fungus based on image data obtained by imaging the first virtual section through the imaging camera,
wherein when the value of the number of fungus is more than a predetermined numerical value, light intensity of the excitation light emitted from the LEDs is decreased, emission intensity of florescence from the fungus is suppressed,
wherein when the average value of luminance is less than a predetermined value, a plurality of times of imaging are conducted during imaging of the next virtual section, imaging data in which luminance is averaged based on a plurality of image data obtained are generated, count of the fungus is conducted based on image data in which luminance is averaged, and
wherein when the value of the number of fungus is less than the predetermined numerical range, light intensity of excitation light emitted from the LEDs is not changed at a time that the average value of luminance is more than the predetermined numerical range, light intensity of the excitation light emitted from the LEDs is increased in a case other than a case that the average value of luminance is more than the predetermined numerical range, and the emission intensity of fluorescence from the fungus is increased.

9. A method for determining a live/dead bacterial state of a fungus by the determination device according to claim 1, comprising:
dropping the specimen in a test tube;
dropping a reagent for staining the fungus in the test tube and sealing and standing the test tube still after stirring;
housing and setting the measurement filter in a filter housing;
connecting the filter housing in which the measurement filter is housed to a top portion of a syringe and forming a communication state between an inner side of the filter housing and an inner side of the syringe;
injecting the specimen in the test tube into the inner side of the syringe;
pressing the specimen containing the fungus in the syringe toward the measurement filter in the filter housing, and thereby filtering and collecting the fungus stained on a surface of the measurement filter;
taking out the measurement filter from the filter housing and putting the measurement filter on the fungus base, and thereby arranging the fungus filtered and collected on the surface of the measurement filter on the fungus base through the measurement filter;
inserting the fungus base in the fungus base holding mechanism of the measurement mechanism provided in the determination device for determining the live/dead bacterial state; and
determining the live/dead bacterial state by utilizing the excitation light irradiation mechanism, the imaging camera, the XY-axes adjustment mechanism, the control portion, and the optical system provided in the determination device and grasping a fungus state as images.

* * * * *